United States Patent [19]
Clark et al.

[11] Patent Number: 6,071,875
[45] Date of Patent: Jun. 6, 2000

[54] TGFα FOR THE TREATMENT OF OCULAR HYPERTENSION AND GLAUCOMA

[75] Inventors: Abbot F. Clark, Arlington; Robert J. Wordinger, Euless, both of Tex.

[73] Assignees: Alcon Laboratories, Inc.; University of North Texas Health Science Center at Fort Worth, both of Fort Worth, Tex.

[21] Appl. No.: 09/308,591
[22] PCT Filed: Nov. 14, 1997
[86] PCT No.: PCT/US97/21055
 § 371 Date: May 19, 1999
 § 102(e) Date: May 19, 1999
[87] PCT Pub. No.: WO98/24468
 PCT Pub. Date: Jun. 11, 1998

Related U.S. Application Data

[60] Provisional application No. 60/033,218, Dec. 4, 1996.
[51] Int. Cl.$^7$ .................................................. A61K 38/00
[52] U.S. Cl. ................................................. 514/2; 514/913
[58] Field of Search ......................................... 514/5, 913

[56] References Cited

U.S. PATENT DOCUMENTS 5,364,374 11/1994 Morrison et al. ...................... 604/272

FOREIGN PATENT DOCUMENTS

WO 94/01124 1/1994 WIPO .

OTHER PUBLICATIONS

Smyth, et al., The Effects of Transferrin Receptor Antibody, Transferrin Receptor Antibody Bound to Pseudomonas Exotoxin and Transforming Growth Factor–α Bound to Pseudomonas Exotoxin on Human Tenon's Capsule Fibroblast Proliferation, *Journal of Ocular Pharmacology*, vol. 8(1):83–90, 1992.

Sarraf, et al., "The Role of Iontophoresis in Ocular Drug Delivery," *Journal of Ocular Pharmacology*, vol. 10(1):69–81, 1994.

Kumar, et al., "Transforming Growth Factor Alpha," *Cell Biology International*, vol. 19(5):373–388, 1995.

*Primary Examiner*—Zohreh Fay
*Attorney, Agent, or Firm*—Sally Yeager

[57] ABSTRACT

Compositions and methods for treating glaucoma and ocular hypertension by using TGFα are disclosed.

3 Claims, No Drawings

TGFα FOR THE TREATMENT OF OCULAR HYPERTENSION AND GLAUCOMA

Priority is claimed from the provisional application, U.S. patent application Ser. No. 60/033,218 filed Dec. 4, 1996.

BACKGROUND OF THE INVENTION

Glaucoma is currently treated using one or more of three strategies to lower the elevated intraocular pressure associated with the disease: with pharmaceuticals (such as beta-blockers, carbonic anhydrase inhibitors, and miotics), with laser trabeculoplasty, and/or with glaucoma filtration surgery. All of these therapies indirectly lower intraocular pressure but do not address the underlying disease process occurring in the trabecular meshwork.

Transforming growth factor alpha (TGFα) is a relative of epidermal growth factor (EGF) and like EGF, it exerts its effects on cells through binding to the EGF receptor. The precise physiological roll of TGFα is still not clear, although it appears to be important in eye and hair follicle development and may play a role in both the immune system and in wound healing. See Kumar, et al., *Cell Biology International*, "Transforming Growth Factor Alpha," 19:5, 373–388, 1995.

SUMMARY OF THE INVENTION

The present invention is directed to methods for treating persons suffering from glaucoma or ocular hypertension through the administration of compositions containing TGFα.

DESCRIPTION OF PREFERRED EMBODIMENTS

Surprisingly, it has been discovered that there is a decrease in TGFα mRNA expression in trabecular meshwork (TM) cells treated with glucocorticoids and in TM cells derived from glaucomatous donors. It has been found that TGFα is an important regulator of TM cell function and, therefore, the lack thereof is believed to be responsible for altered TM cell function leading to the elevated intraocular pressure associated with glaucoma and glucocorticoid-induced ocular hypertension. It is believed that the administration of TGFα to an ocular hypertensive eye will restore normal TM cell function and thereby normalize trabecular outflow resulting in a lowering of intraocular pressure. This treatment is advantageous over prior methods because it interferes with or even prevents the ongoing disease process rather than simply treating the symptoms, particularly elevated intraocular pressure.

As will be appreciated by those skilled in the art, TGFα may be delivered topically, via intraocular (e.g., intracameral) injection or retrograde injection into episcleral veins (see U.S. Pat. No. 5,364,374), through erodible solid ocular inserts, iontophoresis (see Sarraf, et al., *Journal of Ocular Pharmacology*, "The Role of Iontophoresis in Ocular Drug Delivery," 10:1, 69–81, 1994), or by electroporation.

For topical ophthalmic delivery, TGFα may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. Furthermore, the ophthalmic solution may contain a thickener such as hydroxymethylcellulose, hydroxyethylcellulose, hydroxypropylmethylcellulose, methylcellulose, polyvinylpyrrolidone, or the like, to improve the retention of the formulation in the conjunctival sac. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

Whether TGFα is delivered via topical administration or by another previously mentioned route, the pH of the formulation should be about 5–9. The ophthalmic compositions are formulated to provide for an intraocular concentration of about 0.1–100 nanomolar (nM) TGFα, preferably 1–10 nM TGFα. Topical compositions are delivered to the surface of the eye one to four times per day according to the routine discretion of a skilled clinician.

EXAMPLE 1

100 nM TGFα in Viscoat® (available from Alcon Laboratories, Inc., Fort Worth, Tex.) can be used for intraocular injection into the affected eye.

We claim:

1. A method for treating glaucoma or ocular hypertension, which comprises, administering to the eye a pharmaceutically effective amount of TGFα.

2. The method of claim 1 wherein after administration the intraocular concentration of TGFα is between about 0.1 and 100 nM.

3. The method of claim 2 wherein the intraocular concentration of TGFα is between about 1 and 10 nM.

* * * * *